(12) United States Patent
Tung et al.

(10) Patent No.: US 12,012,329 B2
(45) Date of Patent: Jun. 18, 2024

(54) CARBYNE-BASED SENSING DEVICE FOR HIGH SPATIAL RESOLUTION IN DNA SEQUENCING AND BIOMOLECULE CHARACTERIZATION AND METHOD OF FABRICATING THE SAME

(71) Applicants: Steve Tung, Fayetteville, AR (US); Bo Ma, Fayetteville, AR (US); Ty Seiwert, Fayetteville, AR (US)

(72) Inventors: Steve Tung, Fayetteville, AR (US); Bo Ma, Fayetteville, AR (US); Ty Seiwert, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 779 days.

(21) Appl. No.: 17/173,839

(22) Filed: Feb. 11, 2021

(65) Prior Publication Data
US 2021/0253420 A1    Aug. 19, 2021

Related U.S. Application Data

(60) Provisional application No. 62/975,894, filed on Feb. 13, 2020.

(51) Int. Cl.
*B81C 1/00* (2006.01)
*B32B 7/02* (2019.01)
(Continued)

(52) U.S. Cl.
CPC ............ *B81C 1/00071* (2013.01); *B32B 7/02* (2013.01); *B32B 7/12* (2013.01); *B81C 3/001* (2013.01); *C12Q 1/6869* (2013.01)

(58) Field of Classification Search
None
See application file for complete search history.

(56) References Cited

U.S. PATENT DOCUMENTS 6,280,939 B1    8/2001  Allen
7,901,586 B2    3/2011  Yoo
(Continued)

FOREIGN PATENT DOCUMENTS

CN    107167507 A  *  9/2017 ........... H01N 27/327
JP    2002257824 A     9/2002
(Continued)

OTHER PUBLICATIONS

Jeffrey A. Schloss, "How to Get Genomes at One Ten-Thousandth the Cost," Nature Biotechnology, Oct. 2008, p. 1113, vol. 26, No. 10, Nature Publishing Group, US.
(Continued)

*Primary Examiner* — Hsien Ming Lee
(74) *Attorney, Agent, or Firm* — Richard Blakely Glasgow

(57) ABSTRACT

A method of fabricating a sensing device for DNA sequencing and biomolecule characterization including the steps of fabricating a microelectrode chip having a silicon substrate and a silicon nitride diaphragm, attaching a monolayer graphene sheet to the silicon nitride diaphragm, dicing a portion of the monolayer graphene sheet to form a graphene microribbon, converting the graphene microribbon to a graphene nanoribbon, and converting the graphene nanoribbon to a carbyne. A sensing device for DNA sequencing and biomolecule characterization is also disclosed. The sensing device includes a silicon substrate, a cavity in the silicon substrate covered by a silicon nitride layer, microelectrodes attached to the silicon nitride layer, graphene covering the microelectrodes, and carbyne attached to a portion of the silicon nitride layer covering said cavity.

10 Claims, 13 Drawing Sheets

(51) Int. Cl.
    *B32B 7/12*     (2006.01)
    *B81C 3/00*     (2006.01)
    *C12Q 1/6869*     (2018.01)

(56) References Cited

U.S. PATENT DOCUMENTS

| | | | |
|---|---|---|---|
| 9,718,668 | B2 | 8/2017 | Tung et al. |
| 2003/0141189 | A1 | 7/2003 | Lee et al. |
| 2004/0219596 | A1 | 11/2004 | Sundararajan et al. |
| 2007/0082352 | A1 | 4/2007 | Cumpson |
| 2008/0213923 | A1 | 9/2008 | Boland et al. |
| 2009/0227040 | A1 | 9/2009 | Sahin et al. |
| 2009/0305273 | A1 | 12/2009 | Cao et al. |
| 2010/0120023 | A1 | 5/2010 | Sahin et al. |
| 2011/0053805 | A1 | 3/2011 | Riedo et al. |
| 2011/0168562 | A1 | 7/2011 | Nuckolls et al. |
| 2011/0177498 | A1 | 7/2011 | Clarke et al. |
| 2011/0236984 | A1 | 9/2011 | Sun et al. |
| 2013/0213815 | A1 | 8/2013 | Tung et al. |

FOREIGN PATENT DOCUMENTS

| | | | |
|---|---|---|---|
| SG | 173398 | A1 | 8/2011 |
| TW | 200907068 | A | 2/2009 |
| WO | 2008132643 | A1 | 11/2008 |
| WO | 2010062903 | A2 | 6/2010 |
| WO | 2011047582 | A1 | 4/2011 |
| WO | 2011136527 | A2 | 11/2011 |
| WO | 2011142614 | A2 | 11/2011 |
| WO | 2011143340 | A2 | 11/2011 |

OTHER PUBLICATIONS

Michael Zwolak, et al., "Physical Approaches to DNA Sequencing and Detection," Aug. 20, 2007, US.

Vincent Tabard-Cossa, et al., "Noise Analysis and Reduction in Solid-State Nanopores," Nanotechnology, Jun. 29, 2007, p. 1-6, IOP Publishing Ltd., UK.

Jeffrey L. Perry, et al., "Review of Fabrication of Nanochannels for Single Phase Liquid Flow," Microfluid Nanofluid, Dec. 9, 2005, p. 185, Springer-Verlag, US.

Jeroen Haneveld, et al., "Wet Anisotropic Etching for Fluidic 1D Nanochannels," Journal of Micromechanics and Microengineering, Jun. 13, 2003, p. S62, IOP Publishing Ltd., UK.

Arindom Datta, et al., "Nanofluidic Channels by Anodic Bonding of Amorphous Silicon to Glass to Study Ion-Accumulation and Ion-Depletion Effect" Talanta, Jun. 27, 2005, p. 659, vol. 68, Elsevier, US.

Margaret V. Stern, et al., "Nanochannel Fabrication for Chemical Sensors," Journal of Vacuum Science and Technology B, Jul. 2, 1997, p. 2887, vol. 15, AVS, US.

Meint J. De Boer, et al., "Micromachining of Buried Micro Channels in Silicon," Journal of Microelectromechanical Systems, Mar. 2000, p. 94, vol. 9, No. 1, IEEE/ASME, Switz.

Han Cao, et al., "Fabrication of 10nm Enclosed Nanofluidic Channels," Applied Physics Letters, Jul. 1, 2002, p. 174, vol. 81, No. 1, American Inst. of Physics, US.

L. Jay Guo, et al., "Fabrication of Size-Controllable Nanofluidic Channels by Nanoimprinting And Its Application for DNA Stretching" Nano Letters, Dec. 3, 2003, p. 69, vol. 4, No. 1, American Chemical Society, US.

Jonas O. Tegenfeldt, et al., "Micro- and Nanofluidics for DNA Analysis," Anal Bioanal Chem, Mar. 5, 2004, p. 1678, Springer-Verlag, US.

G. Binnig and C.F. Quate, "Atomic Force Microscope," Physical Review letters, Mar. 3, 1986, p. 930, vol. 56, No. 9, American Physical Society, US.

X.N. Xie, et al., "Nanoscale Mat. Patterning and Engineering by Atomic Force Microscopy Nanolithography" Materials Science and Engineering, Nov. 28, 2006, p. 1, vol. R54, Elsevier US.

J.M. Chen, et al., "Electrochemical Synthesis of Polypyrrole within PMMA Nanochannels Produced by AFM mechanical lithography" Synthetic Metals, Oct. 3, 2005, p. 11, Vo. 155, Elsevier, US.

B. Cappella and H. Sturm, "Comparison Between Dynamic Plowing Lithography and Nanoindentation Methods" Journal of Applied Physics, Jan. 1, 2002, p. 506, vol. 91, No. 1, American Inst. of Physics, US.

M. Heyde, et al., "Dynamic Plowing Nanolithography on Polymethylmethacrylate Using An Atomic Force Microscope" Review of Scientific Instruments, Jan. 2001, p. 136, vol. 72, No. 1, Am. Inst. of Physics, US.

Z. Kato, et al., "Nanopatterning on Aluminum Surfaces with AFM Probe," Surface & Coatings Technology, p. 195, 169-170, Elsevier Science B.V., US.

J. Cortes Rosa, et al., "Direct Patterning of Surface Quantum Wells with an Atomic Force Microscope," Applied Physics Letters, p. 2684, vol. 73, No. 18, Am. Inst. of Physics, US.

J. Regul, et al., "Fab. of Quantum Point Contacts by Engraving GaAs/AlGaAs-heterostructures with a Diamond Tip," Appl. Physics Letters 81(11), Sep. 9, 2002, Am Inst of Physics US.

B. Klehn, et al., "Nanolithography with an Atomic Force Microscope . . . " Journal of Applied Physics, Apr. 1, 1999, p. 3897, Vo. 85, No. 7, American Inst. of Physics, US.

Zhi-Qian Wang., et al., "Nanochannels on Silicon Oxide Surface Fabricated by Atomic Force Microscopy," Conference publication—Xiamen, China, Jan. 20, 2010.

Zhi-Qian Wang, et al., "Research on the Atomic Force Microscopy-based Fab of Nanochannels on Silicon Oxide Surfaces" China Sci Bull, Oct. 2010, p. 3466 vol. 55, No. 55, Sci China Press.

T. Maleki, et al., "A Nanofluidic Channel with Embedded Transverse Nanoelectrodes," Nanotechnology 20 (2009) Feb. 16, 2009, p. 1, IOP Publishing Ltd. UK.

John J. Kasianowicz, et al., "Characterization of Individual Polynucleotide Molecules Using a Membrane Channel," Proc Natl Acad Sci USA, Biophysics, Nov. 1996, p. 13770, vol. 93.

James Clarke, et al., "Continuous Base Identification for Single-Molecule Nanopore DNA Sequencing," Nature Nanotechnology, Apr. 2009, p. 265, vol. 4, MacMillan Publishers Ltd. UK.

Z. Wang, et al., "A Nanochannel System Fabricated by MEMS Microfabrication and Atomic Force Microscopy," Proceedings of the 2011 IEEE International, Conference on Nano/Micro Engineered and Molecular Systems, Feb. 20-23, 2011, Taiwan, p. 372-376.

Taylor Busch, Design and Fabrication of Nanofluidic Systems with Integrated Sensing Electrodes for Rapid Biomolecule Characterization, Thesis, May 2013, University of Arkansas.

Shahid Qamar, et al., Can an Atomic Force Microscope Sequence DNA Using a Nanopore?, Biophys. Journal, 94(4), p. 1233-1240 (Feb. 15, 2008).

Nathaniel L. Rosi and Chad A. Mirkin, Nanostructures in Biodiagnostics, Chem. Rev. 2005, 105, p. 1547-1562 (2005).

Karolyn M. Hansen, et al., Cantilever-Based Optical Deflection Assay for Discrimination of DNA Single-Nucleotide Mismatches, Anal. Chem. 2001, 73, p. 1567-1571.

J. M. Kim, et al., Simultaneous Topographic and Fluorescence Imaging of Single DNA Molecules for DNA Analysis with a Scanning Near-Field Optical/Atomic Force Microscope, Anal. Chem. 2001, 73, p. 5984-5991.

Vinod Kumar Khanna, Existing and emerging detection technologies for DNA (Deoxyribonucleic Acid) finger printing, sequencing, bio- and analytical chips: A multidisciplinary development unifying molecular biology, chemical and electronics engineering, Biotechnology Advances 25 (2007), p. 85-98.

Larry J. Kricka, et al., Miniaturized detection technology in molecular diagnostics, Expert Review of Molecular Diagnostics (2005), 5(4), p. 549-559.

Michael D. Garrison, et al., Scanning Probe Microscopy for the Characterization of Biomaterials and Biological Interactions, Annals of the New York Academy of Sciences 831, p. 101-113, (Dec. 1997).

Anne-Sophie Duwez, Molecular cranes swing into action, Nature Nanotechnology, 3, p. 188-189 (2008).

Wen-Hsin Han, et al., Enhanced Recognition of Single-Base Mismatch Using Locked Nucleic Acid-Integrated Hairpin DNA Probes

(56) References Cited

OTHER PUBLICATIONS

Revealed by Atomic Force Microscopy Nanolithography, Anal. Chem. 2010, 82, p. 2395-2400 (2010).
Ozge Akbulut, et al., Application of Supramolecular Nanostamping to the Replication of DNA Nanoarrays, Nano Letters, 7(11), p. 3493-3498 (2007).
Hong Min, et al., Research Progress in Application of Nanomaterials for Deoxyribonucleic Acid Detection, Chinese Journal of Analytical Chemistry, 39(1), p. 146-154 (2011).
Kato, Z., et al., Nanopatterning on aluminum surfaces with AFM probe, Surface and Coatings Technology, 169-170, p. 195-198 (2003).
Rosa, J.C., et al., Direct patterning of surface quantum wells with an atomic force microscope, Applied Physics Letters, vol. 73, No. 18, p. 2684-2686 (Nov. 2, 1998).
D. B. Wells, M. Belkin, J. Comer, and A. Aksimentiev, "Assessing graphene nanopores for sequencing DNA.," Nano Lett., vol. 12, No. 8, pp. 4117-4123, Aug. 2012.
D. Deamer, M. Akeson, and D. Branton, "Three decades of nanopore sequencing," Nat. Biotechnol., vol. 34, No. 5, pp. 518-524, 2016.
C. Jin, H. Lan, L. Peng, K. Suenaga, and S. Iijima, "Deriving Carbon Atomic Chains from Graphene," Phys. Rev. Lett., vol. 102, No. 20, p. 205501, May 2009.
Salman, Z., Nair, A. & Tung, S. One-dimensional carbon chains as electrical sensors for single-stranded DNA. 2017 IEEE 12th Int. Conf. Nano/Micro Eng. Mol. Syst. NEMS 2017 677-681 (2017).
Xie, S.; Jiao, N.; Tung, S.; Liu, L. Fabrication of SWCNT-Graphene Field-Effect Transistors. Micromachines 2015, 6, 1317-1330.

\* cited by examiner

CARBYNE-BASED SENSING DEVICE FOR HIGH SPATIAL RESOLUTION IN DNA SEQUENCING AND BIOMOLECULE CHARACTERIZATION AND METHOD OF FABRICATING THE SAME

CROSS-REFERENCE TO RELATED APPLICATIONS

This application claims the benefit of U.S. Provisional Application No. 62/975,894, entitled "Carbyne Based Nanofluidic Device for High Spatial Resolution in DNA Sequencing and Biomolecule Characterization and Method of Fabricating the Same" and filed on Feb. 13, 2020. The complete disclosure of said provisional application is hereby incorporated by reference.

STATEMENT REGARDING FEDERALLY SPONSORED RESEARCH OR DEVELOPMENT

This invention was made with government support from grant no. 1R21HG010055 awarded by the National Institute of Health. The government has certain rights in the invention.

BACKGROUND OF THE INVENTION

Device-based DNA sequencing has shown tremendous promise in providing a compact sensing platform for portable and cost-effective genomic analysis. New commercial products such as Oxford nanopores have been successfully used to sequence DNA without lengthy sample pretreatments required by the conventional sequencing techniques. In device-based sequencing, single stranded DNA are translocated through a designated sensing area where the instantaneous electrical properties of the DNA are measured. The accuracy of the sequencing result heavily depends on the spatial resolution of the sensing area. In Oxford nanopores, the pore thickness is typically larger than the individual DNA bases. This has led to poor sequencing results due to signal overlapping.

One possible solution for the spatial resolution issue is to use atomically-thin 2D materials such as graphene to construct the sensing area. Graphene nanopores have been successfully fabricated to reduce signal overlapping. However, the results have not been promising due to the fact that signal overlapping in nanopores is controlled by the collinearity of the blockage current in the translocation direction, which still exist even if the pore thickness is smaller than the size of a DNA base. A better solution is to use a 1 D carbon line (carbyne) reduced from 2D graphene to measure the DNA bases through quantum conductance change. In this approach, the width of the sensing area matches the size of the DNA base to achieve high spatial resolution and the measurement is conducted across the DNA backbone to avoid signal overlapping. Numerical simulations have confirmed the benefits of this solution. Of course, in order to utilize the benefits of the carbyne based sensing device, such device must be built for appropriate use. The preferred structure of the carbyne-based sensing device and the preferred method of fabricating the same from commercially available graphene is described herein.

BRIEF SUMMARY OF THE INVENTION

Nanofluidic device-based DNA sequencing using nanopores and nanochannels has shown tremendous promise in providing a rapid, portable, and cost-effective tool for point-of-care genomic analysis. Significant progress in the technique has been made in the last decade resulting in the development of the first commercial nanopore product. However, a number of critical challenges (including poor spatial resolution) remain, preventing nanofluidic device-based DNA sequencing from reaching the much-needed single-base resolution. The present invention utilizes a combination of mechanical dicing, atomic force microscopy (AFM) nanolithography, and transmission electron microscopy (TEM) irradiation to achieve a one-dimensional nanowire sensor to maximize the spatial resolution in DNA sequencing with the ultimate goal of achieving single-base accuracy.

The present invention is directed to a carbyne based sensing device useful for high spatial resolution in DNA sequencing and biomolecule characterization and a method of fabricating the same. The carbyne-based sensing device includes a thin silicon nitride layer deposited on a silicon substrate, wherein the silicon nitride layer acts as a diaphragm for supporting the carbyne and providing a window for TEM processing. The thin silicon nitride layer is deposited on the silicon substrate using chemical vapor deposition (CVD), and a photolithography and KOH wet etching are utilized to achieve the freestanding silicon nitride diaphragm. Chromium and Gold (Cr/AU) are then deposited in sequence on top of the silicon nitride and then patterned in microelectrodes using photolithography to form the contact points for electronic packaging. A piece of monolayer graphene is transferred onto the nitride surface covering the microelectrodes. The carbyne of the device is fabricated from the graphene, which is connected to gold electrodes for electrical accessibility to the carbyne. The preferred novel nano-engineering process of transforming the graphene from a 2D sheet into a single chain of carbon atoms is detailed below, but the process generally involves three major steps: (a) mechanically dicing the graphene into a microribbon, (b) converting the microribbon into a nanoribbon using atomic force microscopy (AFM), and (c) converting the nanoribbon into carbyne using transmission electron microscopy (TEM). These steps and the techniques involved in each are discussed more fully below.

These and other objects, features, and advantages of the present invention will become better understood from a consideration of the following detailed description of the preferred embodiments in conjunction with the drawings as described following:

BRIEF DESCRIPTION OF THE DRAWINGS

FIG. 3A is an image that shows cutting a section of the graphene off the stock. FIG. 3B is an image that shows scooping up a floating graphene by a microelectrode chip. FIG. 3C is an image that shows a microelectrode chip with graphene attached.

FIG. 6A shows gold foil with 2 μm through holes. FIG. 6B shows graphene suspended over a hole in gold foil.

DETAILED DESCRIPTION OF THE INVENTION

With reference to FIGS. 1-12D, the preferred embodiments of the present invention may be described.

Figure 1:
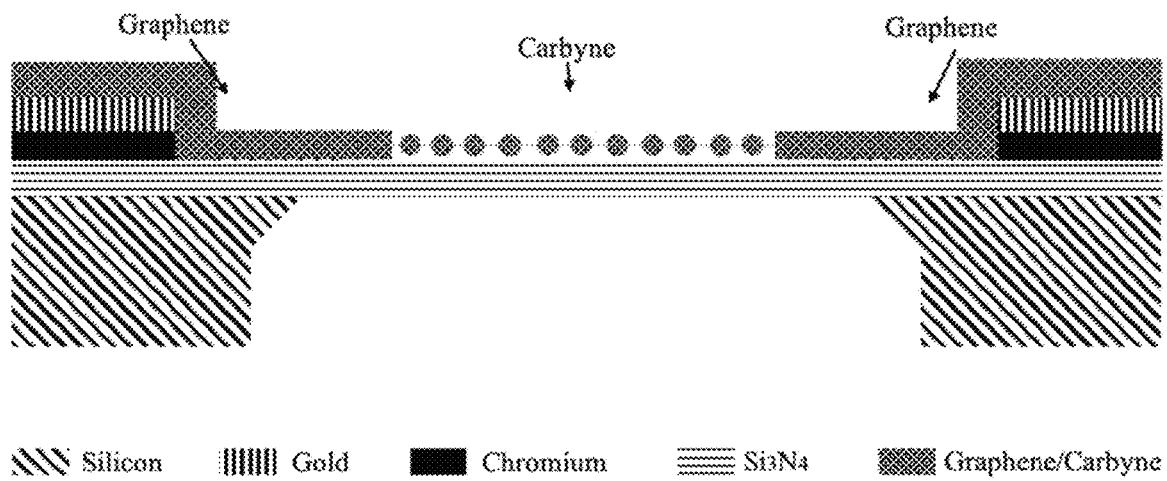
FIG. 1 is a schematic showing a configuration of the carbyne-based sensing device of the present invention.

The present invention is directed to a carbyne-based sensing device useful for high spatial resolution in DNA sequencing and biomolecule characterization and a method of fabricating the same. The carbyne based sensing device of the present invention generally includes: (a) a carbyne fabricated from graphene, (b) chromium and gold electrodes connected to the graphene for electrical accessibility to the carbyne, and (c) a thin silicon nitride layer deposited on a silicon substrate with the silicon nitride layer acting as a diaphragm to support the carbyne, as shown in FIG. 1.

The carbyne device is generally fabricated by depositing the thin silicon nitride layer on the silicon substrate using chemical vapor deposition (CVD), followed by photolithography and KOH wet etch to achieve the freestanding silicon nitride diaphragm. Chromium and Gold (Cr/Au) are then deposited in sequence on top of the silicon nitride and patterned in microelectrodes using photolithography to form the contact points for electronic packaging. A piece of monolayer graphene is transferred onto the silicon nitride surface such that the graphene is also covering the electrodes on the silicon nitride surface. Finally, the single layer graphene is transformed into a carbyne using a process that includes three major steps: (a) mechanically dicing the graphene into a microribbon, (b) converting the microribbon into a nanoribbon using atomic force microscopy (AFM), and (c) converting the nanoribbon into a carbyne using transmission electron microscopy (TEM). Each of these steps and its sub-steps is described more fully below.

Figure 2:
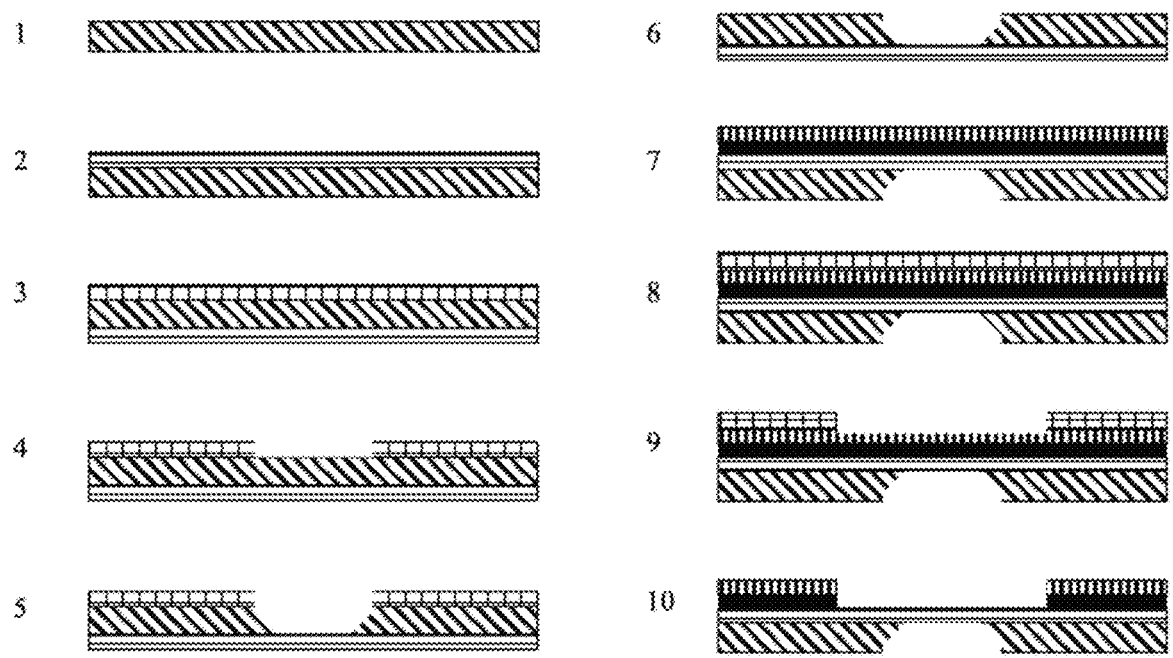
FIG. 2 is a schematic showing the step-by-step process flow of fabricating the nitride diaphragm and microelectrodes of the carbyne-based sensing device of the present invention.

The first step in the overall process is to fabricate the silicon nitride diaphragm with integrated microelectrodes. A standard MEMS microfabrication process is used. It consists of thin film deposition, double-sided photolithography, and wet bench processing. The process flow is shown step-by-step in FIG. 2. A layer of silicon nitride ($Si_3N_4$) is deposited on silicon wafer using CVD technology (FIG. 2, steps 1-2). Photolithography is then carried out on the backside to transfer the diaphragm pattern to the substrate (FIG. 2, steps 3-4). Wet KOH etching opens a cavity in the silicon substrate and stops at the nitride layer to form a diaphragm structure (FIG. 2, steps 5-6). Next, 15 nm Chromium (Cr) and 45 nm gold (Au) are deposited on the nitride in sequence (FIG. 2, step 7). Photolithography is carried out to align the microelectrode pattern with the diaphragm structure (FIG. 2, steps 8-9). After a wet bench process, the wafer is immersed in gold and chromium etchant sequentially to realize the microelectrodes (FIG. 2, step 10). Finally, the silicon wafer is diced into individual devices.

Figure 3A:
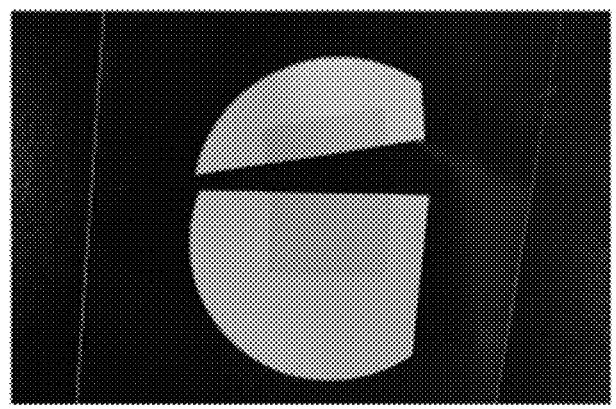
FIGS. 3A-3C show the process of transferring graphene onto a microelectrode chip.
Figure 3B:
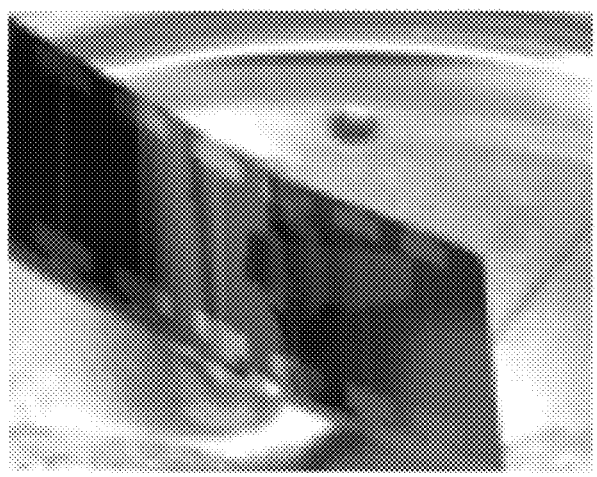
Figure 3C:
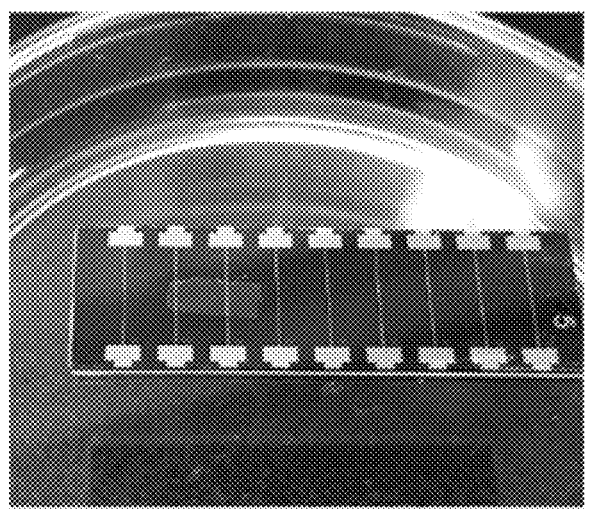

Once the silicon nitride diaphragm with integrated microelectrodes has been produced, a monolayer graphene sheet is attached to the microelectrode-diaphragm chip. The monolayer graphene may be, for example, one sold by Graphenea (as shown for example in FIG. 3A). The gray area in the center on FIG. 3A is the graphene monolayer covered by a PMMA protection layer, and the background white material is the polymer substrate. The attaching process is described as follows. First, wet the polymer substrate around (not directly on) the graphene/PMMA composite layer with a small amount of water and let sit for 5 minutes to promote graphene separation. Then, slowly dip the graphene/PMMA layer on polymer substrate into deionized (DI) water and let sit for 20 minutes. The polymer substrate will sink to the bottom while the graphene/PMMA composite layer will float to the surface. Next, place the silicon nitride chip in a holder and lower it into DI water away from the floating graphene/PMMA layer. Use tweezers to maneuver floating graphene/PMMA into place, and then slowly raise the chip to scoop up the floating graphene/PMMA. FIG. 3B demonstrates the process of using a microelectrode chip to scoop up a floating graphene sheet in DI water. As noted, a micro tweezer is usually used to gently maneuver the graphene onto the chip and align with the electrodes. In any event, great caution needs to be used since this process is nearly irreversible. The goal is to attach the graphene to the chip where the microelectrodes and diaphragm meet. The chip should then be held vertically for at least one minute to allow water to drain. To dry the chip, blow dry with nitrogen and air dry for thirty minutes. Then anneal the chip on a hot plate at 150° C. for one hour. The chip should be stored in a vacuum for twenty-four hours to promote adhesion between the graphene/PMMA and silicon nitride substrate. Then, the chip is soaked in acetone for one hour and then IPA for another hour to remove PMMA. Then the chip is blow dried with nitrogen gas. Finally, anneal in nitrogen for 2 hours at 450° C. if the solvent cannot completely remove PMMA. FIG. 3C shows the microelectrode chip with the graphene attached on the left end. At this point, the attached graphene is ready for transformation into the carbyne.

Figure 4:
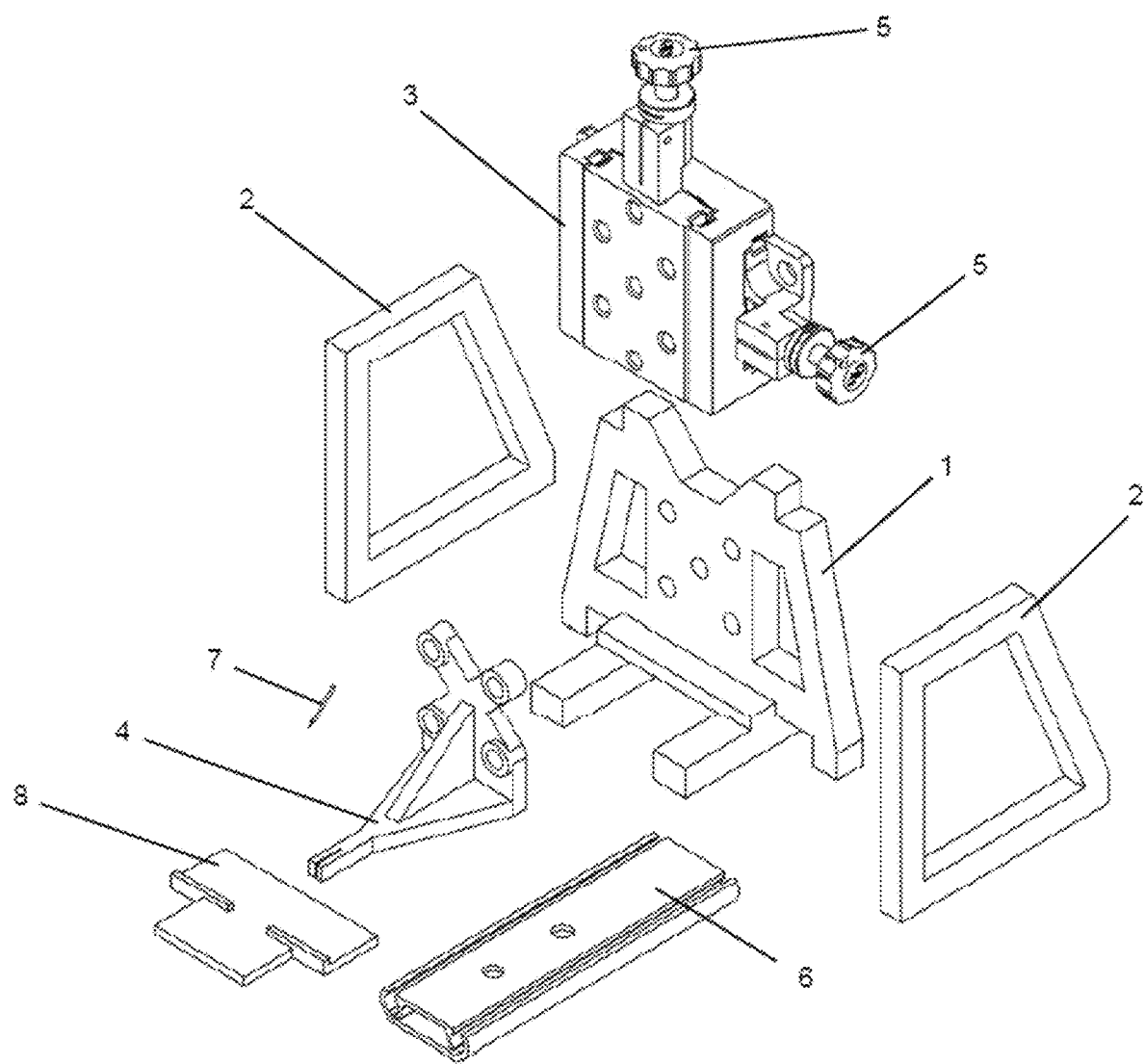
FIG. 4 is an exploded view of the dicing station of the present invention.
Figure 5A:
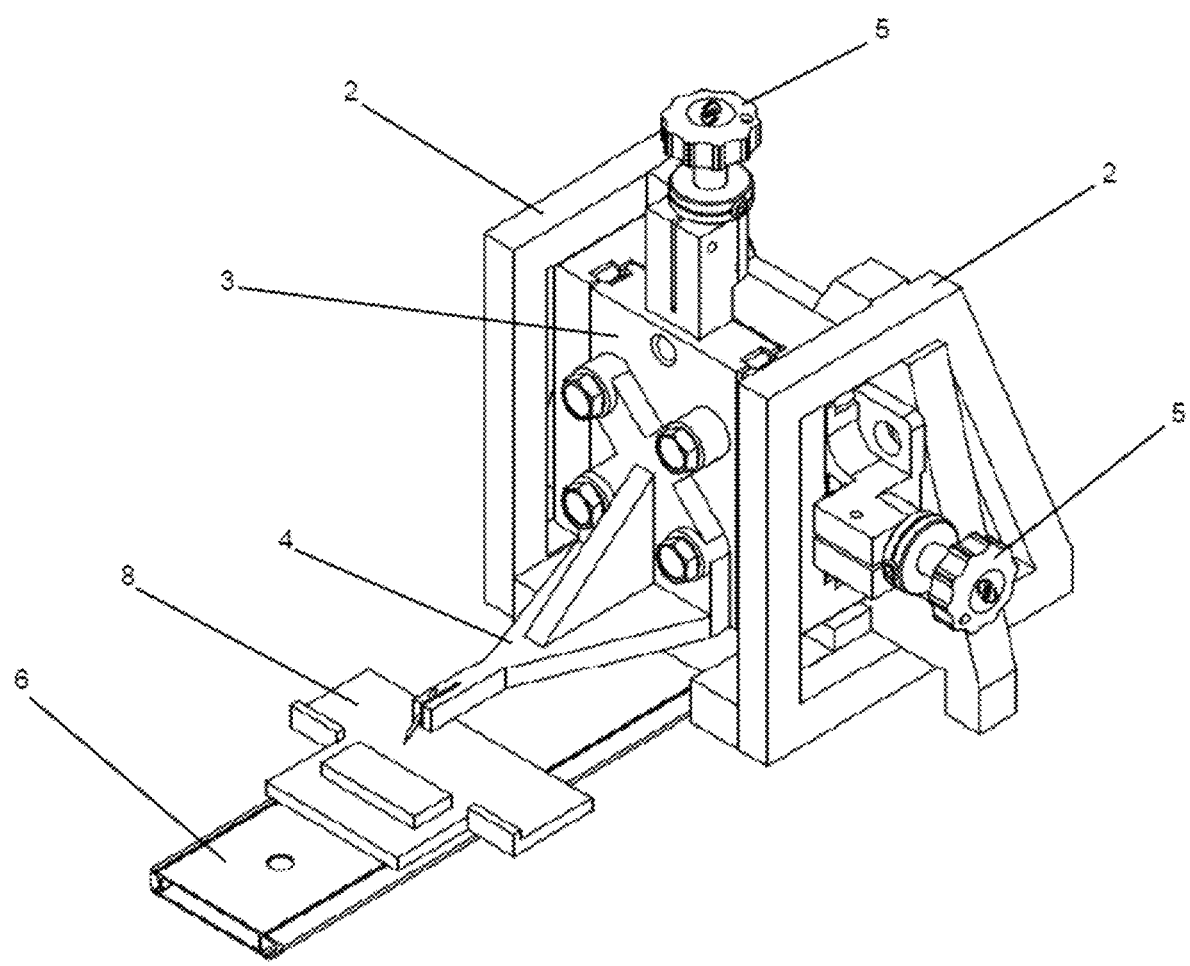
FIG. 5A is a perspective view of the dicing station of the present invention.

The first step in transforming the single layer graphene into a carbyne is mechanically dicing the graphene into a microribbon. At this step, a micro dicing station to mechanically machine a graphene sheet is utilized. The preferred structure of the dicing station is described more fully below. The dicing station is used to cut the graphene sheet into a microribbon, and the station includes a micro positioning stage, a diamond tipped scribe, a 3D printed support, and an inspection microscope. More specifically, as shown in FIGS. 4 and 5A, the dicing station preferably includes a backplate 1, two side bars 2, a microstage 3, a blade holder 4, adjustment screws or knobs 5, a linear slide 6, a diamond tipped scribe 7, and a chip holder 8. The station is capable of achieving a 10 μm-wide graphene microribbon, which is within the operating range of the AFM nanolithography. The developed mechanical dicing station is simple, low-cost, and capable of providing a reliable and accurate mechanical cut.

At the second step, AFM nanolithography is used to convert the graphene microribbon into a nanoribbon. The graphene microribbon is mechanically reduced to nanometer range using developed AFM nanolithography techniques. The AFM is equipped with a diamond tipped AFM probe and a lithography compatible system. The procedure and parameters for operating the AFM based nanolithography are established for dicing consistency and repeatability.

At the third step of converting the single layer graphene into a carbyne, TEM electron irradiation is used to convert the nanoribbon into the carbyne. At this step, the graphene nanoribbon is positioned at the center of the electron beam exposure to reduce its width by removing carbon atoms at the edges, allowing the width of the nanoribbon to be reduced to a single chain of carbon atoms. The feasibility of using TEM to convert a graphene into a freestanding chain of carbon atoms has been previously reported. However, this reported technique does not dictate the physical location of the fabricated carbyne. The present approach of achieving a carbyne by reducing a nanoribbon not only allows the resultant carbyne to be accurately located in a device but also integrated with contact electrodes.

Experimental Results

Figure 5B:
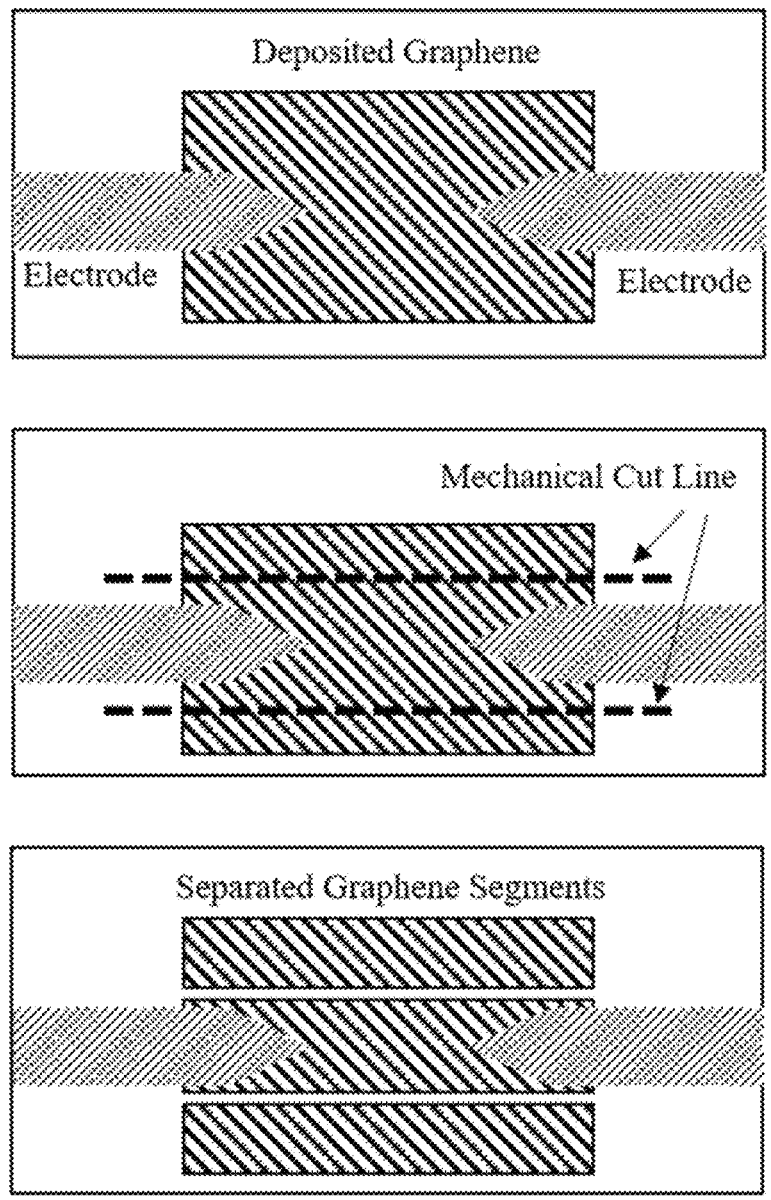
FIG. 5B is a schematic showing the step-by-step process for graphene dicing in the present invention.
Figure 7:
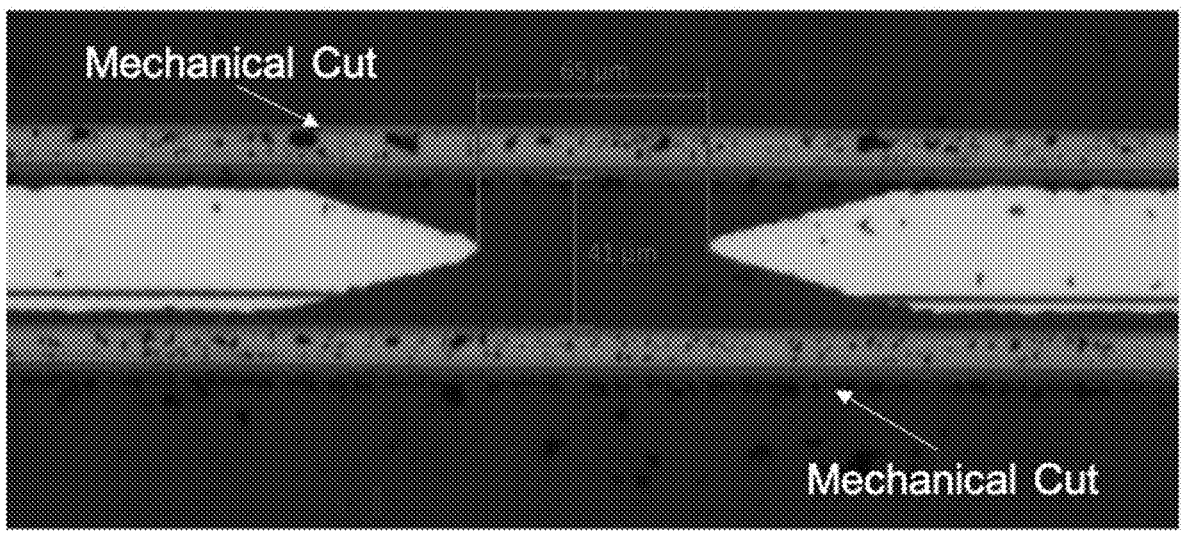
FIG. 7 is an image showing a graphene microribbon between two triangular microelectrodes on a silicon substrate.

Step 1—Graphene Microribbon Fabrication: An exploded view of the dicing station is shown in FIG. 4, which shows the dicing station as an assembly of eight items. A 2D XY micro stage 3 is the center core of the station for holding and positioning the diamond dicing tip. Rotating two knobs 5 changes the lateral and vertical position of the XY stage. The backplate 1, side bars 2, blade holder 4, and chip holder 8 are supporting structures and were fabricated in-house using 3D printing for the experimental tests. The other parts (i.e., the microstage 3, the knobs 5, and the diamond tip 7) were purchased from commercial venders. The dicing station also includes a linear or extension slide 6. FIG. 5A shows an assembled dicing station with a silicon microelectrode chip mounted on the chip holder 8, while FIG. 5B shows the graphene dicing scheme step-by-step. A successful dicing operation results in a continuous graphene microribbon linking two triangular microelectrodes. FIG. 7 demonstrates a 41 μm wide graphene microribbon realized by the micro dicing station. More recent work has reduced the width to about 10 μm.

Step 2—AFM nanolithography for fabricating a graphene nanoribbon: An Agilent 5500 AFM was utilized to reduce the width of the graphene microribbon to the nanometer scale. A DNISP all-diamond cantilever (Veeco, NY) was used in the cutting operation due to its large force capability (Force constant=225 N/m). Initial calibration cuts were conducted to determine the optimal force and cutting speed to achieve the desired cutting depth. The force-depth calibration results are provided below. The calibrated parameters were used to realize a 500 nm wide graphene nanoribbon. The result is shown below. The electrical properties of the graphene were characterized before, during, and after each cutting process to monitor the change in electrical continuity of the graphene between the microelectrodes. The measurements are shown below.

Figure 8A:
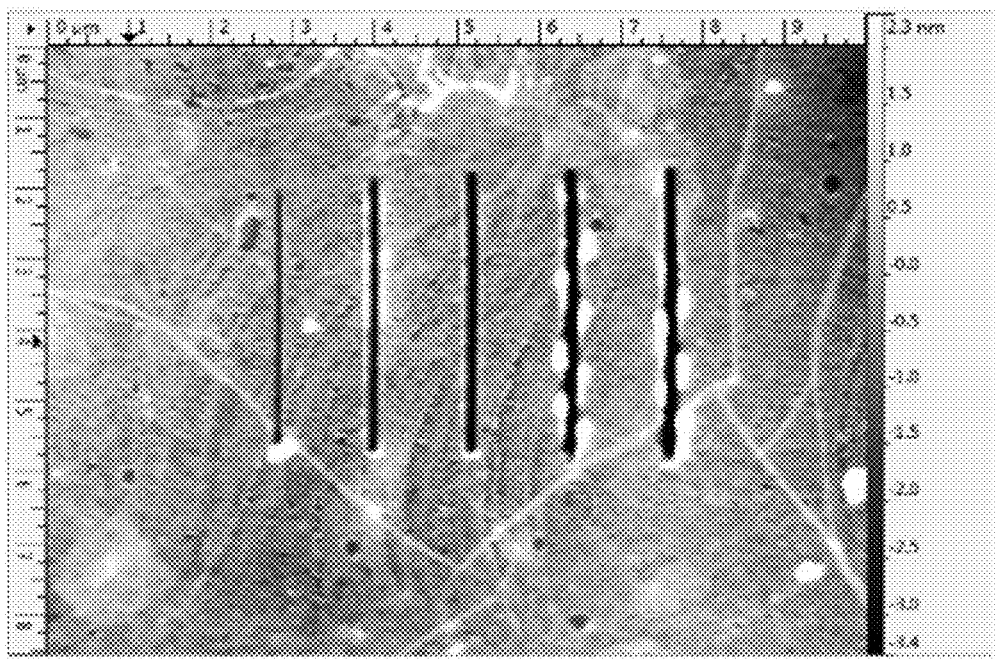
FIG. 8A is an image showing an AFM-measured topography of four cutting lanes in graphene when different tip forces are used.
Figure 8B:
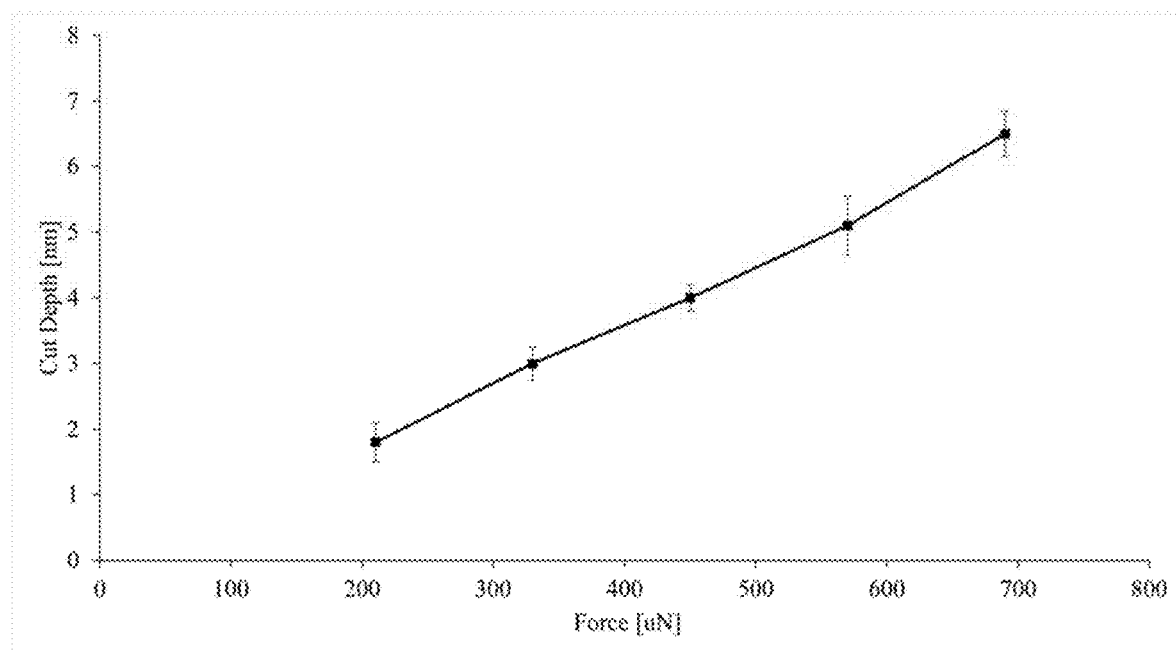
FIG. 8B is a graph showing the relationship between tip force and resulting cutting depth.
Figure 9A:
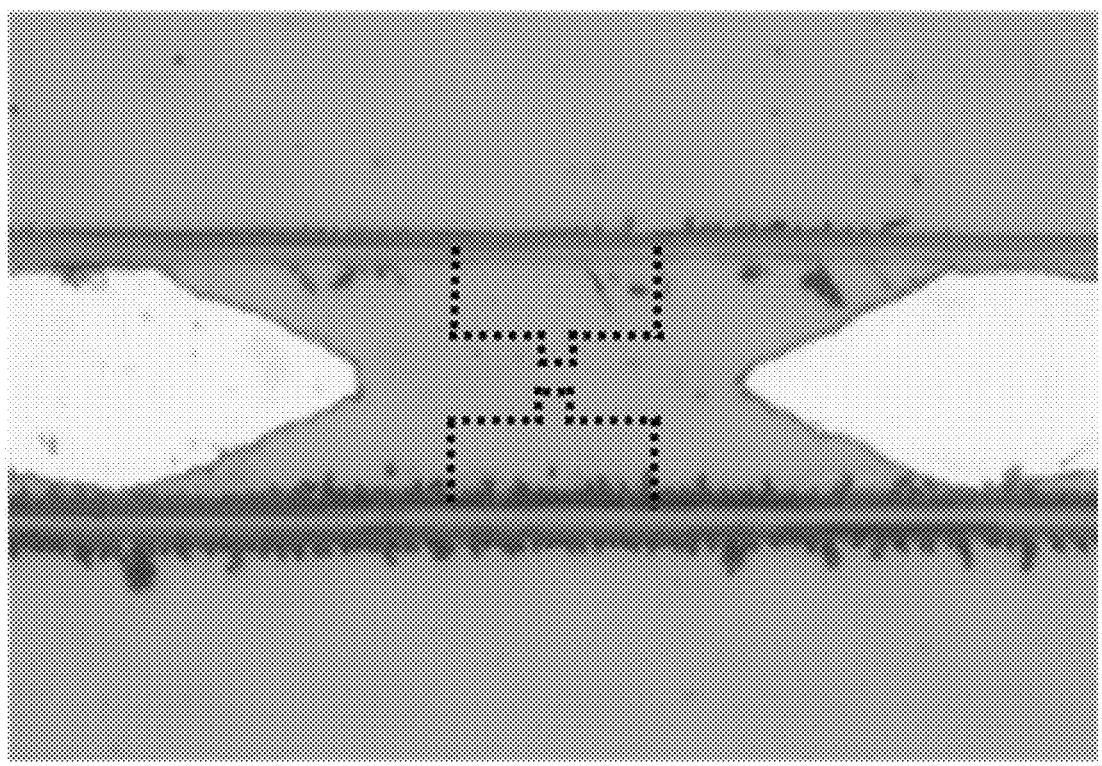
FIG. 9A is an image showing the graphene microribbon subjected to AFM nanolithography with the cutting path indicated.
Figure 9B:
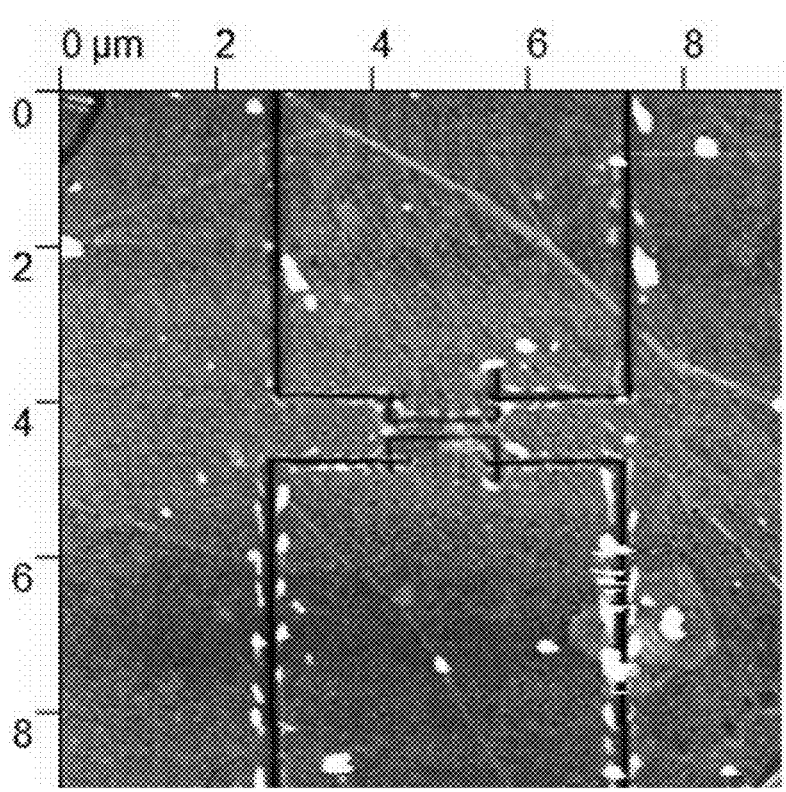
FIG. 9B is an AFM image of the nanoribbon achieved by AFM cutting.
Figure 10:
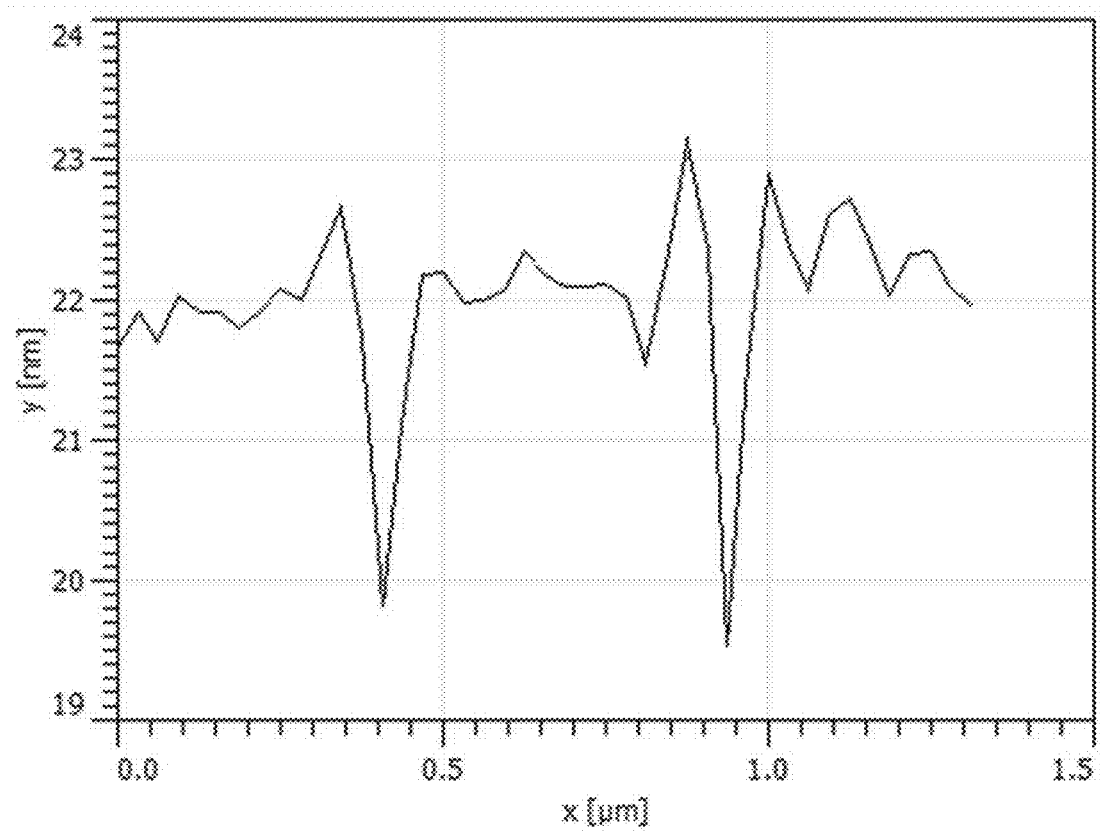
FIG. 10 is a graph showing a height profile across a graphene nanoribbon.

Force-vs-depth calibration was carried out to determine the optimized control parameters for using AFM nanolithography to machine a graphene sheet on a silicon substrate. As shown in FIG. 8A, the AFM tip force increases gradually from the leftmost lane to the rightmost. FIG. 8B demonstrates a linear relationship between force and depth. This result allowed the inventors to carefully select a tip force in order to cut through the graphene layer without damaging the substrate underneath. The inventors determined that a cutting speed of 6 μm/s and a tip force of 30 μN were the optimized combination for machining graphene. FIGS. 9A-B demonstrates using AFM nanolithography to achieve a graphene nanoribbon. FIG. 10 indicates the width of the nanoribbon is about 500 nm (or 0.5 μm).

Figure 11:
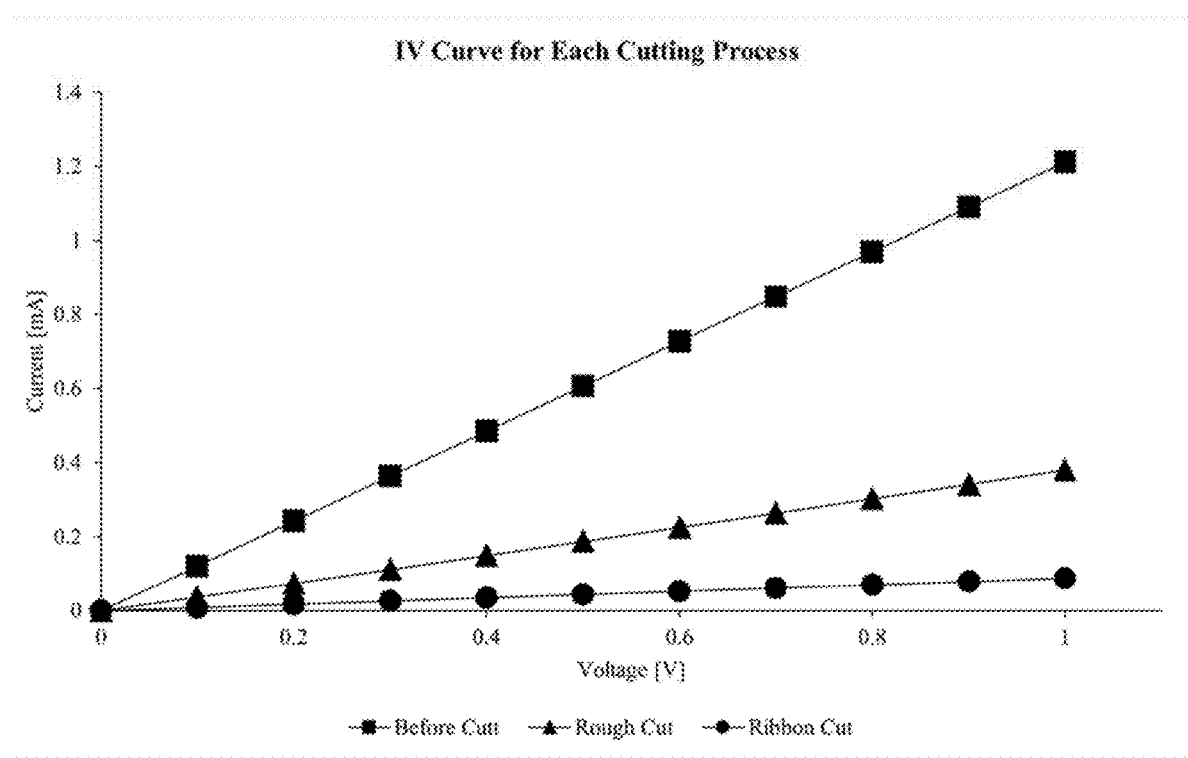
FIG. 11 is a graph showing I-V characteristics of graphene after it is deposited (top line-before cut), after it is cut into a microribbon (middle line-rough cut), and after it is cut into a nanoribbon (bottom line-ribbon cut).
Figure 12A:
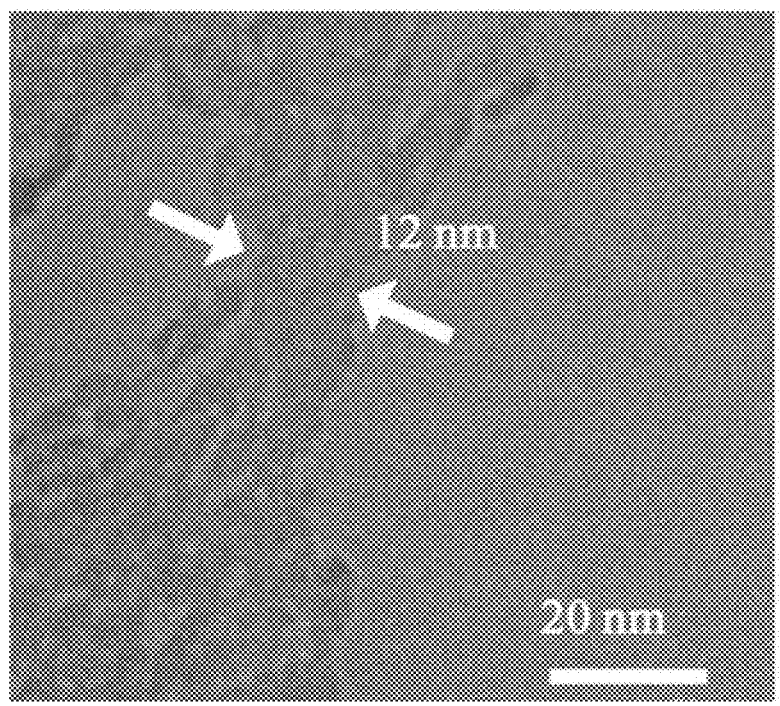
FIGS. 12A-12D are images showing how the use of TEM irradiation reduces the width of the graphene nanoribbon.
Figure 12B:
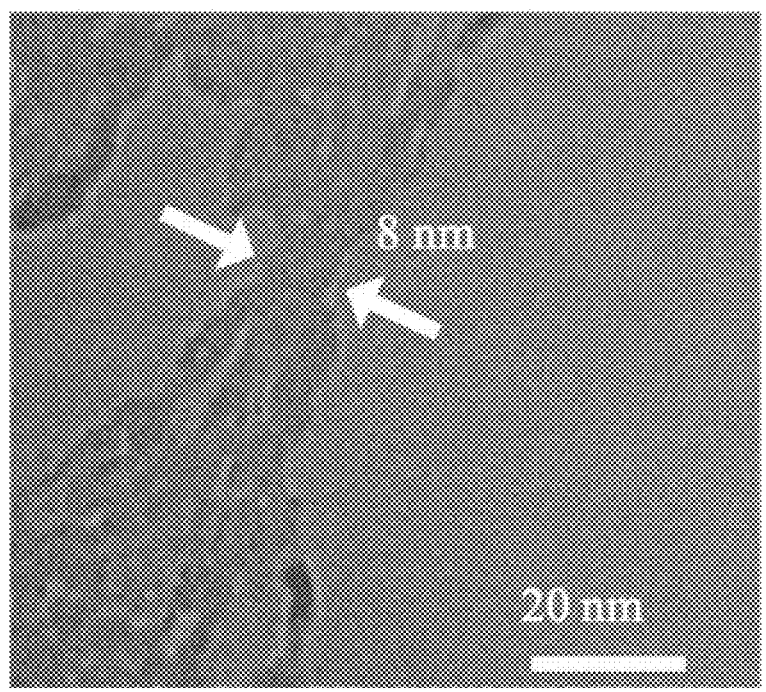
Figure 12C:
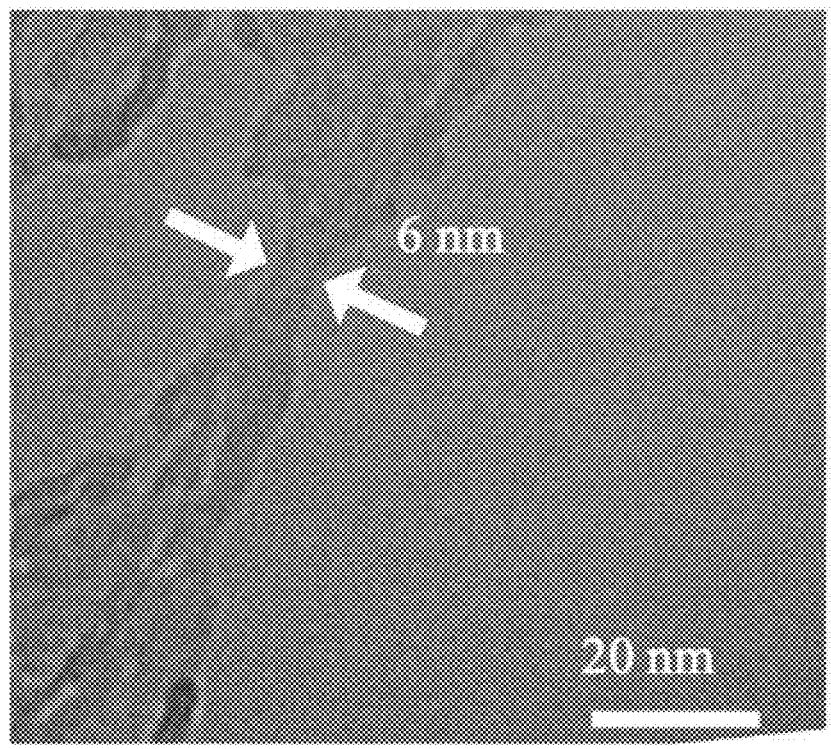
Figure 12D:
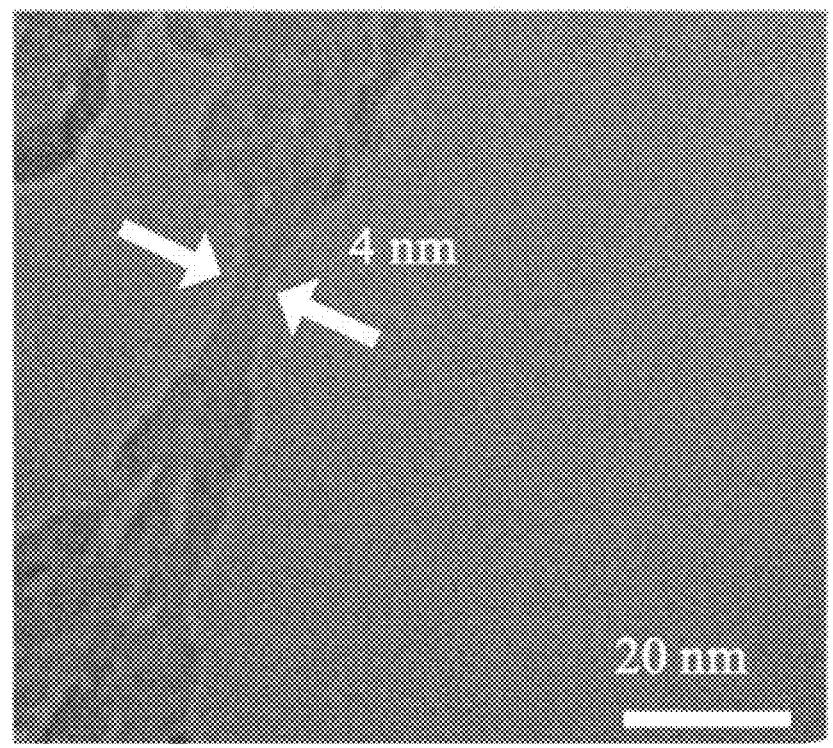

The current-vs-voltage (I-V) curves of the graphene after it is first deposited on the microelectrodes (line with squares), after the mechanical cutting step (line with triangles), and after the AFM cutting step (line with circles) are shown in FIG. 11. All three curves demonstrate a liner relationship, indicating an ohmic behavior of the graphene. This is consistent with previous work. The slopes of the three lines show a consistent reduction in electrical conductivity when the widths of the graphene are reduced. This is also expected since the width of a resistor is inversely proportional to the electrical resistance. In the uncut state, the graphene has an electrical resistance of about 1 kOhms. In the final nanoribbon, the resistance has increased to about 10 kOhms.

Figure 6A:
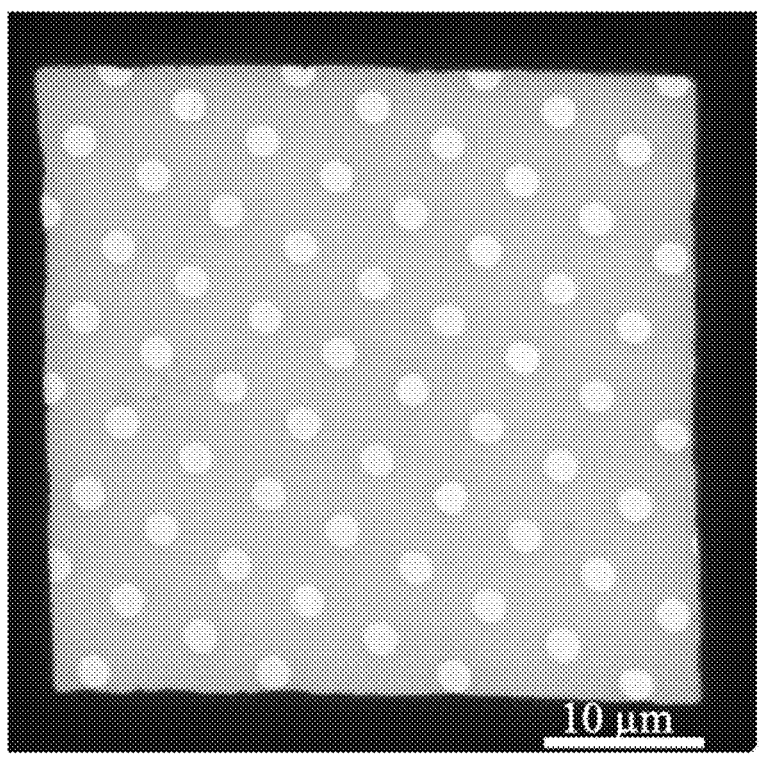
FIGS. 6A-6B are images showing graphene on a TEM grid.
Figure 6B:
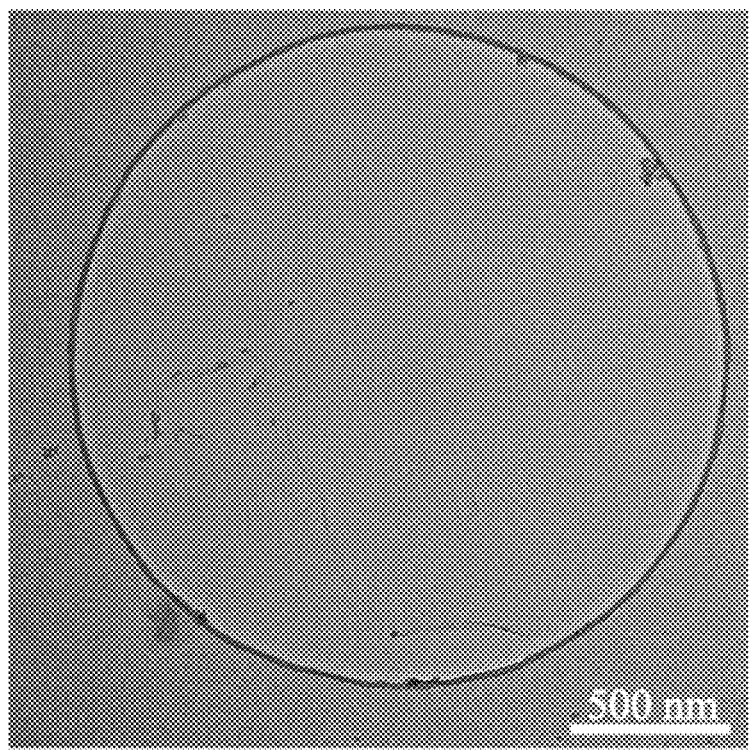

Step 3—TEM electron beam irradiation for fabricating a carbyne line: Preliminary proof-of-concept work was conducted using a JEM 1011 TEM. TEM grid coated with a monolayer of graphene was purchased from Graphenea (Cambridge, MA) for this work. This grid was fabricated from copper and covered by an additional layer of Quantifoil® gold mesh to support the graphene. The gold mesh is 50 nm thick and each circular hole has a diameter of 2 μm. As shown in FIG. 6A, the black square frame is the copper TEM grid. Inside the black square is the Quantifoil® gold mesh which is semi-transparent and the 2 μm holes are 4 μm apart. FIG. 6B is a TEM image showing a monolayer graphene suspended over a hole. TEM irradiation is used to continuously remove carbon atoms from a graphene nanoribbon in the center of the electron beam exposure. The TEM electron energy was set at 100 keV. The beam spot size was set to profile 1 and the magnification was set at 600,000×. After 10 minutes of irradiation, a 12 nm wide graphene nanoribbon was eventually narrowed down to 4 nm.

FIGS. 12A-D show the result of the feasibility study of using TEM irradiation to reduce the width of graphene nanoribbon. The inventors successfully reduced the width from 12 to 4 nm in a 10 minutes continuous process. As previously explained, due to the limitation of the TEM used (JEM 1011), the inventors were not able to further reduce the graphene nanoribbon to a single carbon chain. The inventors are currently exploring the use of a higher resolution TEM (Titan 800-3000) to achieve this goal.

Resolution limitation of the JEM 1011 prevented the inventors from visualizing the atomic structure of the graphene nanoribbon. Further investigation will focus on irradiating the 4 nm graphene nanoribbon using a TEM Titan 800-3000 at University of Arkansas Nano-Bio Materials Characterization Facility. Its sub-nanometer imaging capability will assist the fabrication work to achieve atomic level accuracy. Titan 800-3000 is the state-of-the-art TEM at the University of Arkansas. With an attached EDAX module, this TEM can provide a very high spatial resolution for imaging and elemental analysis. Titan 800-3000 can be operated using the same control parameters developed on JEM 1011 for carbon atom removal, but the facility can deliver a 100× better image resolution. The inventors will use the Titan 800-3000 to achieve a carbyne device from the graphene microribbon device.

The inventors are currently developing the process flow for fabricating silicon nitride chips with integrated microelectrodes. With these chips, the inventors plan to repeat the graphene sheet transfer and width reducing processes to realize a graphene microribbon on a silicon nitride diaphragm. The inventors expect to use focused ion beam (FIB) technology to thin down the thickness of the diaphragm for better TEM imaging and irradiation.

The present invention may provide benefits in (a) rapid biocontamination inspection for food safety, environmental safety, boarder security; (b) rapid human DNA identification for social security, public safety, and homeland security; (c) rapid DNA verification of gene-edited cells for human health and medical safety; and (d) rapid DNA recognition for disease identification, spreading tracing, and prevention. Advantages of the present invention include (a) single-base accuracy in DNA sequencing; (b) direct electrical sensing without the need for complex sample pretreatments; (c) the sensor integration process is compatible with existing MEMS techniques; and (d) the sensor is designed for portable systems and on-site analysis.

REFERENCES

1. D. B. Wells, M. Belkin, J. Comer, and A. Aksimentiev, "Assessing graphene nanopores for sequencing DNA.," Nano Lett., vol. 12, no. 8, pp. 4117-23, August 2012.
2. D. Deamer, M. Akeson, and D. Branton, "Three decades of nanopore sequencing," Nat. Biotechnol., vol. 34, no. 5, pp. 518-524, 2016.
3. C. Jin, H. Lan, L. Peng, K. Suenaga, and S. Iijima, "Deriving Carbon Atomic Chains from Graphene," Phys. Rev. Lett., vol. 102, no. 20, p. 205501, May 2009.
4. Salman, Z., Nair, A. & Tung, S. One-dimensional carbon chains as electrical sensors for single-stranded DNA. 2017 IEEE 12th Int. Conf. Nano/Micro Eng. Mol. Syst. NEMS 2017 677-681 (2017). doi:10.1109/NEMS.2017.8017112
5. Xie, S.; Jiao, N.; Tung, S.; Liu, L. Fabrication of SWCNT-Graphene Field-Effect Transistors. Micromachines 2015, 6, 1317-1330.

The present invention has been described with reference to certain preferred and alternative embodiments that are intended to be exemplary only and not limiting to the full scope of the present invention.

We claim:

1. A method of fabricating a sensing device for DNA sequencing and biomolecule characterization comprising the steps of:
   fabricating a microelectrode chip comprising a silicon substrate and a silicon nitride diaphragm;
   attaching a monolayer graphene sheet to said silicon nitride diaphragm;
   dicing a portion of said monolayer graphene sheet to form a graphene microribbon;
   converting said graphene microribbon to a graphene nanoribbon; and
   converting said graphene nanoribbon to a carbyne.

2. The method of claim 1, wherein said the step of fabricating a microelectrode chip comprises the steps of:
   depositing a layer of silicon nitride on a first surface of said silicon substrate;
   performing photolithography on a second surface of said silicon substrate;
   performing potassium hydroxide etching to create a cavity in said second surface of said silicone substrate, wherein said silicon nitride diaphragm covers an end of said cavity;
   depositing a layer of chromium and a layer of gold on said layer of silicon nitride;
   performing photolithography on said second surface of said silicon substrate; and
   immersing said silicon substrate in gold etchant and immersing said silicon substrate in a chromium etchant to form microelectrodes.

3. The method of claim 1, wherein said step of converting said graphene microribbon to a graphene nanoribbon comprises the step of performing atomic force microscopy nanolithography.

4. The method of claim 1, wherein said step of converting said graphene nanoribbon to a carbyne comprises the step of performing electron irradiation.

5. The method of claim 2, wherein said step of depositing a layer of silicon nitride on a first surface of said silicon substrate comprises the step of using chemical vapor deposition.

6. The method of claim 2, wherein said step of attaching a monolayer graphene sheet to said silicon nitride diaphragm comprises the step of attaching said monolayer graphene sheet at a position where said microelectrodes contact said silicon nitride diaphragm.

7. The method of claim 1, wherein said step of dicing a portion of said monolayer graphene sheet to form said graphene microribbon comprises the step of using a dicing station.

8. The method of claim 1, wherein said step of converting said graphene nanoribbon to said carbyne comprises the step of using transmission electron microscopy.

9. A sensing device for DNA sequencing and biomolecule characterization comprising:
   a silicon substrate;
   a cavity in said silicon substrate covered by a silicon nitride layer;
   microelectrodes attached to said silicon nitride layer;
   graphene covering said microelectrodes; and
   carbyne attached to a portion of said silicon nitride layer covering said cavity.

10. The sensing device of claim 9, wherein said graphene is a monolayer.

* * * * *